US005719127A

United States Patent [19]
Atkinson et al.

[11] Patent Number: 5,719,127
[45] Date of Patent: Feb. 17, 1998

[54] MODIFIED COMPLEMENT SYSTEM REGULATORS

[75] Inventors: John P. Atkinson, St. Louis; Dennis Hourcade, Creve Coeur; Malgorzata Krych, St. Louis, all of Mo.

[73] Assignee: Washington University, St. Louis, Mo.

[21] Appl. No.: 688,675

[22] Filed: Jul. 30, 1996

Related U.S. Application Data

[62] Division of Ser. No. 210,266, Mar. 18, 1994, Pat. No. 5,545,619, which is a continuation of Ser. No. 695,514, May 3, 1991, abandoned.

[51] Int. Cl.$^6$ .................................................. A61K 38/36
[52] U.S. Cl. ............................................ 514/12; 530/350
[58] Field of Search ............................. 514/12; 530/350

[56] References Cited

U.S. PATENT DOCUMENTS

| | | |
|---|---|---|
| 4,883,784 | 11/1989 | Kaneko ........................... 514/8 |
| 5,212,071 | 5/1993 | Fearon et al. ................. 435/69.1 |
| 5,256,642 | 10/1993 | Feason et al. .................... 514/8 |
| 5,472,939 | 12/1995 | Feason et al. .................... 514/8 |

FOREIGN PATENT DOCUMENTS

| | | |
|---|---|---|
| 8901041 | 2/1989 | WIPO . |
| WO 89/09220 | 10/1989 | WIPO . |
| 9102002 | 2/1991 | WIPO . |
| WO 91/05047 | 4/1991 | WIPO . |
| 9118097 | 11/1991 | WIPO . |
| PCT/JP93/00207 | 9/1993 | WIPO . |

OTHER PUBLICATIONS

Lublin et al. J. Exp. Med. 165: 1731–1736 (1987).
Adams et al., "Contribution of the Repeating Domains of Membrane Cofactor Protein (CD46) of the Complement System to Ligand Binding and Cofactor Activity," J. Immunology 147:3005–3011 (1991).
Atkinson and Farries, "Separation of self from non–self in the complement system," Immun. Today 8:212–215 (1987).
Ballard, et al., "*A Polymorphism of the Complement Regulatory Protein MCP (Membrane Cofactor Protein or gp–45–70)*$^{1}$" J. of Immun. 138:3850–3855 (1987).
Ballard, et al., "Biochemical Characterization of Membrane Cofactor Protein of the Complement System," J. of Immun. 141:3923–3929 (1988).
Birmingham and Cosio, "Characterization of the Baboon Erthrocyte C3b–Binding Protein," J. of Immun. 142:3140–3144 (1989).
Birmingham et al., "Primary Sequence of an Alternatively Spliced Form of CR1," J. of Immunol. 153:691–700 (1994).
Bora, et al., "Structural Gene for Human Membrane Cofactor Protein (MCP) of Complement Maps to Within 100 kb of the 3' End of the C3b/C4b Receptor Gene," J. Exp. Med. 169:597–602 (1989).
Brauer, et al., "Use of C6–Deficient Rats to Evaluate the Mechanism of Hyperacute Rejection of Discordant Cardia Xenografts," J. of Immunol. 151:7240–7248 (1993).

Caras, et al., "Signal for Attachment of a Phospholipid Membrane Anchor in Decay Accelerating Factor," Science 238:1280–1283 (1987).
Caras, I.W., et al., "Cloning of decay–accelerating factor suggests novel use of splicing to generate two proteins," Nature (1987) 325:545–549.
Carel, et al., "Structural Requirements for C3d,g/Epstein–Barr Virus Receptor (CR2)/(CD21) Ligand Binding, Internalization and Viral Infection," J. Biol. Chem. 265:12293–12299 (1990).
Chung, L.P. et al., "Molecular cloning and characterization of the cDNA coding for C4b–binding protein, a regulatory protein of the classical pathway of the human complement system," Biochem. J. 230:133–141 (1985).
Cole, J.L., et al., "Identification of an additional class of C3–binding membrane proteins of human peripheral blood leukocytes and cell lines," Proc. Natl. Acad. Sci. USA 82:859–863 (1985).
Coyne, et al., "Mapping of Epitopes Glycosylation Sites, and Complement Regulatory Domains in Human Decay Accelerating Factor," J. Immunology 149:2906–2913 (1992).
Dykman, et al., "Polymorphism of human erythrocyte C3b/C4b receptor," Proc. Natl. Acad. Sci. USA 80:1698–1702 (1983).
Dykman, et al., "Structural Heterogeneity of the C3b/C4b Receptor (CR1) on Human Peripheral Blood Cells," J. Exp. Med. 157:2160–2165 (1983).
Farries, et al., "Competition for Binding Sites on C3b by CR1, CR2, MCP, Factor B and Factor H," Complement Inflamm 7:30–41 (1990).
Fodor, et al., "A Novel Bifunctional Chimeric Complement Inhibitor That Regulates C3 Convertase and Formation of the Membrane Attack Complex," J. of Immunol. 155:4135–4138 (1995).
Ghebrehiwet, B., et al., "Purification and Immunochemical Characterization of Soluble Forms of the Two Types of C10 Receptors," Complement and Complement Receptors Abstract 2751 A275 (1994).

(List continued on next page.)

*Primary Examiner*—Stephen Walsh
*Assistant Examiner*—Karen E. Brown
*Attorney, Agent, or Firm*—Arnall Golden & Gregory, LLP

[57] ABSTRACT

Analogs of regulators of complement activation (RCA) proteins which have altered specificities and affinities for the targets C3b and/or C4b are described. These analogs are obtained by substituting amino acids which effect the binding of these proteins, identified as amino acids 35, 64–65, 92–94 (C4b) and the sequence S-T-K-P-(P-I-C)-Q (C3b) in the CR1 protein can be transferred to corresponding regions of CR1 or of additional members of the RCA family. Analogs can also be designed by substituting amino acids which affect the binding of these proteins into homologous regions of noncorresponding SCRs of CR1 or other family members.

10 Claims, 3 Drawing Sheets

OTHER PUBLICATIONS

Goujet–Zalc, et al., "Marmoset Red Blood Cell Receptor for Membrane–Associated Complement Components Is Not Related to Human CR1: Partial Characterization of the C3–Binding Proteins Responsible for the Spontaneous Rosette Formation between Marmoset Red Blood Cells and Human Leukocytes," Cell. Immun. 109:282–294 (1987).

Hillarp, A., and Dhalback, B., "Cloning of cDNA coding for the β chain of human complement component C4b–binding protein: Sequence homology with the α chain," Proc. Natl. Acad. Sci. USA 87:1183–1187 (1990).

Himmelfarb, et al., "Soluble complement receptor 1 inhibits both complement and granulocyte activation during ex vivo hemodialysis," J. Lab. Clin. Med. 126:392–400 (1995).

Hogg, N., et al., "Identification of an anti–monocyte monoclonal antibody that is specific for membrane complement receptor type one ($CR_1$)," Eur. J. Immunol. 14:236–243 (1984).

Holers, et al., "Human C3b–and C4b–regulator proteins: a new multi–gene family," Immun. Today 6:188–192 (1985).

Hourcade, D., et al., "Analysis of the Human Regulators of Complement Activation (RCA) Gene Cluster with Yeast Artificial Chromosomes (YACs)," Genomics 12:289–300 (1992).

Hourcade, et al., "Duplication and Divergence of the Amino–terminal Coding Region of the Complement Receptor 1 (CR1) Gene," J. of Biol. Chem. 265:974–980 (1990).

Hourcade, et al., "Identification of an Alternative Polyadenylation Site in the Human C3b/C4b Receptor (Complement Receptor Type 1) Transcriptional Unit and Prediction of a Secreted Form of Complement Receptor Type 1," J. Exp. Med., 168:1255–1270 (Oct., 1988).

Hourcade and Atkinson, "The Regulators of Complement Activation (RCA) Gene Cluster," Progress in Immun. VII:171–174 (1989).

Janatova, et al., "Disulfide Bonds Are Localized within the Short Consensus Repeat Units of Complement Regulatory Proteins: C4b–Binding Protein," Biochem. 28:4754–4761 (1989).

Joyner et al., "Production of a mutation in mouse En–2 gene by Homologous recombination in embryonic stem cells," Nature 338:1513–156 (1989).

Kalli, et al., "Interaction of iC3b with Recombinant Isotypic and Chimeric Forms of CR2," J. Immunology 147:590–594 (1991).

Kalli, et al, "Mapping of the C3b–binding Site of CR1 and Construction of a $(CR1)_2$–$F(ab')_2$ Chimeric Complement Inhibitor," J. Exp. Med. 174:1451–1460 (1991).

Kim, "Isolation and identification of Trophoblast Lymphocyte Cross–reactive (TLX) Antigens from Human Lymphocytes," J. of Biol. Chem. 264:9780–9784 (1989).

Klickstein, L.B., et al., "Human C3b/C4b Receptor (CR1)," J. Exp. Med. 165:1095–1112 (1987).

Klickstein, et al., "Identification of Distinct C3b and C4b Recognition Sites in the Human C3b/C4b Receptor (CR1, CD35) by Deletion Mutagenesis," J. Exp. Med., 168:1699–1717 (Nov., 1988).

Krych, et al, "Analysis of the Functional Domains of Complement Receptor Type 1 (C3b/C4b Receptor; CD35) by Substitution Mutagenesis*," The Journal of Biochemical Chemistry, 269(18):13273–13278 (May, 1994).

Krych, et al., "Identification of a C3b Binding Domain of Human Complement C3b/C4b Receptor (CR1)," FASEB J. 4(7) Abstract 2853 (1990).

Krych, et al., "Identification of the Sequence Effecting C3b but not C4b Binding in C3b/C4b Binding Site in CR1," Molecular Immunology, 33(1): abstract number 128 (Jun., 1996).

Krych, et al., "Localization of Decay Accelerating Activity in Complement Receptor Type 1 (CR1, CD35)", The 9th International Congress of Immunology Abstract Book, p. 17 (Jul. 23–29, 1996).

Krych, et al., "On the Mechanism of Decay Accelerating Activity (DAA) of Complement Receptor Type One (CR1, CD35) for the alternative Pathway (AP) Convertase," Molecular Immunology, 33(1): abstract number 129 (Jun., 1996).

Kunkel, T.A., et al., "Rapid and Efficient Site–Specific Mutagenesis without Phenotypic Selection," Methods Enzymol 154:367–382 (1987).

Liszewski, M. Kathryn, et al., "Control of the Complement System," Adv. in Immunol. 61:201–283 (1996).

Lovell–Badge, "Introduction of DNA into embryonic stem cells," Teratocarcinomas and embryonic stem cells, a practical approach, (ed. E.J. Robertson, IRL Press, 1987) 153–182.

Lublin, D.M., et al., "Molecular Cloning and Chromosomal Localization of Human Membrane Cofactor Protein (MCP)," J. Exp. Med. 168:181–194 (1988).

Lublin and Atkinson, "Decay–Accelerating Factor: Biochemistry, Molecular Biology, and Function," Ann. Rev. Immunol. 7:35–58 (1989).

Lublin and Atkinson, "Decay–Accelerating Factor and Membrane Cofactor Protein," Curr. Topics in Micro. and Immun. 153:123–145 (1989).

Makrides, S.C., et al., "Cell Surface Expression of the C3b/C4b Receptor (CR1) Protects Chinese Hamster Ovary Cells from Lysis by Human Complement," J. Biol. Chem. 267:24754–24761 (1992).

McNearney, et al., "Membrane Cofactor Protein of Complement is Present on Human Fibroblast, Epithelial, and Endothelial Cells," J. Clin. Invest. 84, 1–8 (1989).

Medof, M.E., et al., "Cloning and characterization of cDNAs encoding the complete sequence of decay–accelerating factor of human complement," Proc. Natl. Acad. Sci. USA (1987) 84:2007–2011.

Moore, "CRRP: A Guinea Pig Protein, Identified by Sequence Homology to Human CR1, Which Contains Two Short Consensus Repeat Motifs and Appears Not To Be Transmembrane or Secreted," J. of Immunol. 147:3615–3622 (1991).

Moore, M.D., et al., "Molecular cloning of the cDNA encoding the Epstein–Barr virus/C3d Receptor (complement receptor type 2), of human B lymphocytes," Proc. Natl. Acad. Sci. USA 84:9194–9198 (1987).

Nickells, et al., "Identification of Complement Receptor Type 1–Related Proteins on Primate Erythrocytes," J. of Immunol. 154:2829–2837 (1995).

Nickells, et al., "Identification of 65–70kDa CR1 Molecules from Primate E," Complement and Complement Receptors FASEB Journal 8(4) Abstract 2749, (1994).

O'Shea, J.J., et al., "Evidence for Distinct Intracellular Pools of Receptors for C3b and C3bi in Human Neutrophils," J. Immunol. 134:2580–2587 (1985).

Ogata, et al., "Murine C4b–Binding Protein," J. Immunology 150:2273–2280 (1993).

Post, et al., "Membrane Cofactor Protein of the Complement System: Alternative Splicing of Serine Threonin Proline-rich Exons and Cytoplasmic Tails Produces Multiple Isoforms that Correlate with Protein Phenotype," J. Exp. Med. 174:93–102 (1991).

Potter, et al., "Enhancer-dependent expression of human K immunoglobulin genes introducted into mouse pre-B lymphocytes by electroporation," Proc. Natl. Acad. Sci. USA 81:7161–7165 (1984).

Pruitt, et al., "The Effect of Soluble Complement Receptor Type 1 on Hyperacute Xenograft Rejection," Transplantation 52:868–873 (1991).

Purcell, et al., "The human cell-surface glycoproteins Huly-m5, membrane co-factor protein (MCP) of the complement system, and trophoblast leucocyte-common (TLX) antigen, are CD46," Immun. 70:155–161 (1990).

Remington: The Science and Practice of Pharmacy Nineteenth Edition, vols. I and II, 19th ed. (1995) Table of Contents, XV–XVI and VII–VIII.

Ripoche, J., et al., "The complete amino acid sequence of human complement factor H," Biochem. J. 249:593–602 (1988).

Seya, T., et al., "Purification and Functional Analysis of the Polymorphic Variants of the C3b/C4b Receptor (CR1) and Comparison with H, C4b-Binding Protein (C4bp), and Decay Acceleration Factor (DAF)," J. Immunology 135:2661–2667 (1985).

Seya and Atkinson, "Functional properties of membrane cofactor protein of complement," Biochem. J. 264:581–588 (1989).

Seya, et al., "Distribution of membrane cofactor protein of complement on human peripheral blood cells. An altered form is found on granulocytes," Eur. J. Immunol. 18:1289–1294 (1988).

Seya, et al., "Purification and Characterization of a Membrane Protein (gp45–70) that is a Cofactor for Cleavage of C3b and C4b," J. Exp. Med. 163:837–855 (1986).

Seya, "membrane cofactor protein (MCP)," Complement Regulation (1988) Abstract Only.

Southern and Berg, "Transformation of Mammalian Cells to Antibiotic Resistance with a Bacterial Gene Under Control of the SV40 Early Region Promoter," J. Mol. Appl. Gen. 1:327–341 (1982).

Stafford, et al., "Normal polymorphic variations and transcription of the decay accelerating factor gene in paroxysmal nocturnal hemoglobinuria cells," Proc. Natl. Acad. Sci. USA 85:880–884 (1988).

Subramanian, V., et al., "Ligand Binding by Chimpanzee Erythrocyte Complement Receptor," Complement and Complement Receptors, FASEB Journal 8(5): Abstract 4447 (1994).

Weiss, J.J., et al., "Structure of the Human B Lymphocyte Receptor for C3d and the Epstein–Barr Virus and Relatedness to Other Members of the Family of C3/C4 Binding Proteins," J. Exp. Med. 167:1047–1066 (1988).

Wong and Fearon, "p65: A C3b-Binding Protein on Murine Cells that Shares Antigenic Determinants with the Human C3b Receptor (CR1) and is Distinct from Murine C3b Receptor," J. of Immun. 134:4048–4056 (1985).

Wong, "Structural and Functional Correlation of the Human Complement Receptor Type 1," J. of Investigative Dermatology 94:64S–67S (1990).

Wong, et al., "Identification of a partial cDNA clone for the human receptor for complement fragments C3b/C4b," Proc. Natl. Acad. Sci. USA 82:7711–7715 (1985).

Yu, et al., "Identification of a Third Component of Complement-binding Glycoprotein of Human Platelets," J. Clin. Invest. 78:494–501 (1986).

Zimmer and Gruss, "Production of chimaeric mice containing embryonic stem (ES) cells carrying a homoeobox Hox 1.1 allele mutated by homologous recombination," Nature 338:150–153 (1989).

Hourcade et al., Adv. Immunol. (1989) 45:381–416.

Krych et al., Proc. Natl. Acad. Sci. (May 15, 1991) 88, 4353–4357.

Wong et al., J. Immunol. (1991) 146:656–662.

Ross et al., Adv. Immunol. (1985) 37:217–267.

Platt et al., Immunol. Today (1990) 11:450–457.

Yeh et al., J. Immunol. (1991) 146:250–256.

Weissman et al., Science (1990) 249:146–151.

Kotwal et al., Nature (1988) 335:176–178.

McNearney, J. Exp. Med. (1987) 166:1525–1535.

FIG. 3

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
( A ) LENGTH: 8 amino acids (B) TYPE: amino acid
(C) STRANDEDNESS: single
(D) TOPOLOGY: linear (ii) MOLECULE TYPE: peptide (xi) SEQUENCE DESCRIPTION: SEQ ID NO:1:

Ser Thr Lys Pro Pro Ile Cys Gln
1               5

(2) INFORMATION FOR SEQ ID NO:2:

(i) SEQUENCE CHARACTERISTICS:
    (A) LENGTH: 8 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:2:

Asp Asn Glu Thr Pro Ile Cys Asp
1               5

(2) INFORMATION FOR SEQ ID NO:3:

(i) SEQUENCE CHARACTERISTICS:
    (A) LENGTH: 8 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:3:

Asp Lys Lys Ala Pro Ile Cys Asp
1               5

(2) INFORMATION FOR SEQ ID NO:4:

(i) SEQUENCE CHARACTERISTICS:
    (A) LENGTH: 8 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:4:

Ser Asp Pro Leu Pro Glu Cys Arg
1               5

(2) INFORMATION FOR SEQ ID NO:5:

(i) SEQUENCE CHARACTERISTICS:
    (A) LENGTH: 7 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:5:

Ser Asp Pro Leu Pro Glu Cys
1               5

(2) INFORMATION FOR SEQ ID NO:6:

(i) SEQUENCE CHARACTERISTICS:
    (A) LENGTH: 8 amino acids (B) TYPE: amino acid
(C) STRANDEDNESS: single
(D) TOPOLOGY: linear (ii) MOLECULE TYPE: peptide (xi) SEQUENCE DESCRIPTION: SEQ ID NO:6:

Ser Gly Lys Pro Pro Ile Cys Glu
1               5

(2) INFORMATION FOR SEQ ID NO:7:

(i) SEQUENCE CHARACTERISTICS:
    (A) LENGTH: 8 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:7:

Asn Ser Ser Val Pro Val Cys Glu
1               5

(2) INFORMATION FOR SEQ ID NO:8:

(i) SEQUENCE CHARACTERISTICS:
    (A) LENGTH: 8 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Modified-site
    (B) LOCATION: 3
    (D) OTHER INFORMATION: /note= "K/R"

(ix) FEATURE:
    (A) NAME/KEY: Modified-site
    (B) LOCATION: 6
    (D) OTHER INFORMATION: /note= "I/L/V"

(ix) FEATURE:
    (A) NAME/KEY: Modified-site
    (B) LOCATION: 8
    (D) OTHER INFORMATION: /note= "Q/N"

(xi) SEQUENCE DESCRIPTION: SEQ ID NO:8:

Ser Thr Lys Pro Pro Ile Cys Gln
1               5

(2) INFORMATION FOR SEQ ID NO:9:

(i) SEQUENCE CHARACTERISTICS:
    (A) LENGTH: 8 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Modified-site
    (B) LOCATION: 1
    (D) OTHER INFORMATION: /note= "D/E"

(ix) FEATURE:
    (A) NAME/KEY: Modified-site
    (B) LOCATION: 2
    (D) OTHER INFORMATION: /note= "N/Q"

(ix) FEATURE:

(A) NAME/KEY: Modified-site
(B) LOCATION: 3
(D) OTHER INFORMATION: /note= "E/D"

( i x ) FEATURE:
(A) NAME/KEY: Modified-site
(B) LOCATION: 6
(D) OTHER INFORMATION: /note= "I/L/V"

( i x ) FEATURE:
(A) NAME/KEY: Modified-site
(B) LOCATION: 8
(D) OTHER INFORMATION: /note= "D/E"

( x i ) SEQUENCE DESCRIPTION: SEQ ID NO:9:

```
Asp  Asn  Glu  Thr  Pro  Ile  Cys  Asp
1                  5
```

(2) INFORMATION FOR SEQ ID NO:10:

( i ) SEQUENCE CHARACTERISTICS:
(A) LENGTH: 60 amino acids
(B) TYPE: amino acid
(C) STRANDEDNESS: single
(D) TOPOLOGY: linear ( i i ) MOLECULE TYPE: peptide ( x i ) SEQUENCE DESCRIPTION: SEQ ID NO:10:

```
Gln  Cys  Asn  Ala  Pro  Glu  Trp  Leu  Pro  Phe  Ala  Arg  Pro  Thr  Asn  Leu
1                  5                       10                      15

Thr  Asp  Glu  Phe  Glu  Phe  Pro  Ile  Gly  Thr  Tyr  Leu  Asn  Tyr  Glu  Cys
                   20                      25                      30

Arg  Pro  Gly  Tyr  Ser  Gly  Arg  Pro  Phe  Ser  Ile  Ile  Cys  Leu  Lys  Asn
              35                      40                      45

Ser  Val  Trp  Thr  Gly  Ala  Lys  Asp  Arg  Cys  Arg  Arg
         50                      55                      60
```

(2) INFORMATION FOR SEQ ID NO:11:

( i ) SEQUENCE CHARACTERISTICS:
(A) LENGTH: 60 amino acids
(B) TYPE: amino acid
(C) STRANDEDNESS: single
(D) TOPOLOGY: linear ( i i ) MOLECULE TYPE: peptide ( x i ) SEQUENCE DESCRIPTION: SEQ ID NO:11:

```
His  Cys  Gln  Ala  Pro  Asp  His  Phe  Leu  Phe  Ala  Lys  Leu  Lys  Thr  Gln
1                  5                       10                      15

Thr  Asn  Ala  Ser  Asp  Phe  Pro  Ile  Gly  Thr  Ser  Leu  Lys  Tyr  Glu  Cys
                   20                      25                      30

Arg  Pro  Glu  Tyr  Tyr  Gly  Arg  Pro  Phe  Ser  Ile  Thr  Cys  Leu  Asp  Asn
              35                      40                      45

Leu  Val  Trp  Ser  Ser  Pro  Lys  Asp  Val  Cys  Lys  Arg
         50                      55                      60
```

(2) INFORMATION FOR SEQ ID NO:12:

( i ) SEQUENCE CHARACTERISTICS:
(A) LENGTH: 62 amino acids
(B) TYPE: amino acid
(C) STRANDEDNESS: single
(D) TOPOLOGY: linear ( i i ) MOLECULE TYPE: peptide ( x i ) SEQUENCE DESCRIPTION: SEQ ID NO:12:

Lys Ser Cys Arg Asn Pro Pro Asp Pro Val Asn Gly Met Val His Val
1               5                   10                  15

Ile Lys Gly Ile Gln Phe Gly Ser Gln Ile Lys Tyr Ser Cys Thr Lys
            20                  25                  30

Gly Tyr Arg Leu Ile Gly Ser Ser Ala Thr Cys Ile Ile Ser Gly
            35              40                  45

Asp Thr Val Ile Trp Asp Asn Glu Thr Pro Ile Cys Asp Arg
        50              55                  60

( 2 ) INFORMATION FOR SEQ ID NO:13:

( i ) SEQUENCE CHARACTERISTICS:
        ( A ) LENGTH: 62 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

Lys Ser Cys Lys Thr Pro Pro Asp Pro Val Asn Gly Met Val His Val
1               5                   10                  15

Ile Thr Asp Ile Gln Val Gly Ser Arg Ile Asn Tyr Ser Cys Thr Thr
            20                  25                  30

Gly His Arg Leu Ile Gly His Ser Ser Ala Glu Cys Ile Leu Ser Gly
            35              40                  45

Asn Ala Ala His Trp Ser Thr Lys Pro Pro Ile Cys Gln Arg
        50              55                  60

( 2 ) INFORMATION FOR SEQ ID NO:14:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 4
        ( D ) OTHER INFORMATION: /note= "I/L/V"

( i x ) FEATURE:
        ( A ) NAME/KEY: Modified-site
        ( B ) LOCATION: 6
        ( D ) OTHER INFORMATION: /note= "G/S/A"

( i x ) FEATURE:
        ( A ) NAME/KEY: Modified-site
        ( B ) LOCATION: 7
        ( D ) OTHER INFORMATION: /note= "I/L/V"

( i x ) FEATURE:
        ( A ) NAME/KEY: Modified-site
        ( B ) LOCATION: 8
        ( D ) OTHER INFORMATION: /note= "F/Y"

( i x ) FEATURE:
        ( A ) NAME/KEY: Modified-site
        ( B ) LOCATION: 10
        ( D ) OTHER INFORMATION: /note= "D/E"

( i x ) FEATURE:
        ( A ) NAME/KEY: Modified-site
        ( B ) LOCATION: 11
        ( D ) OTHER INFORMATION: /note= "I/L/V"

( i x ) FEATURE:
    ( A ) NAME/KEY: Modified-site
    ( B ) LOCATION: 12
    ( D ) OTHER INFORMATION: /note= "F/Y"

( i x ) FEATURE:
    ( A ) NAME/KEY: Modified-site
    ( B ) LOCATION: 15
    ( D ) OTHER INFORMATION: /note= "F/Y"

( i x ) FEATURE:
    ( A ) NAME/KEY: Modified-site
    ( B ) LOCATION: 17
    ( D ) OTHER INFORMATION: /note= "I/L/V"

( i x ) FEATURE:
    ( A ) NAME/KEY: Modified-site
    ( B ) LOCATION: 19
    ( D ) OTHER INFORMATION: /note= "G/S/A"

( x i ) SEQUENCE DESCRIPTION: SEQ ID NO:14:

```
Cys Pro Pro Leu Asn Ser Leu Phe Gly Asp Leu Phe Cys Gly Phe Gly
1               5                   10                  15

Leu Cys Ser Trp Pro Cys
            20
```

( 2 ) INFORMATION FOR SEQ ID NO:15:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:15:

```
Asp Thr Val Ile
1
```

( 2 ) INFORMATION FOR SEQ ID NO:16:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:16:

```
Asn Ala Ala His
1
```

( 2 ) INFORMATION FOR SEQ ID NO:17:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:17:

```
Asp Asp Phe Met
1
```

( 2 ) INFORMATION FOR SEQ ID NO:18:

( i ) SEQUENCE CHARACTERISTICS:

( A ) LENGTH: 4 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:18:

Arg Asn Pro Pro
1

MODIFIED COMPLEMENT SYSTEM REGULATORS

This application is a Divisional of Ser. No. 08/210,266 filed on Mar. 18, 1994, by John P. Atkinson, Dennis Hourcade, and Malgorzata Krych for "Modified Complement System Regulators", now U.S. Pat. No. 5,545,619, which is a continuation of application Ser. No. 07/695,514 filed May 3, 1991 now abandoned.

TECHNICAL FIELD

The invention relates to regulation of the complement system employing modified proteins of the gene cluster which encodes regulators of complement activation (RCA). More specifically, it concerns analogs of proteins of this system which have modified binding specificities and affinities.

BACKGROUND ART

The complement system serves to aid in the removal of foreign substances and of immune complexes from animal hosts. A recent summary of the nature of this system and its regulation was published by Hourcade, D., et al., *Advances in Immunol* (1989) 45:381–416, which is incorporated herein by reference.

Briefly, as set forth in this review, the complement system generates, either by a "classical pathway" or an "alternative pathway," the important protein C3b which binds to target immune complexes or foreign substances and marks them for destruction or clearance. C3b is generated from its precursor C3 by the proteolytic enzymes collectively designated "C3 convertase." One form of C3 convertase is generated in the classical pathway by the association of the proteins C4b and C2a. The other form is generated in the alternative pathway by association of C3b and Bb. Both C3 convertases can associate with an additional C3b subunit to form the C5 convertases, C3bBbC3b and C4bC2aC3b, both of which are active in the production of the C5–C9 membrane attack complex which can cause cell lysis, and in the production of C5a, a major pro-inflammatory agent. Thus, both C3b, and less directly, C4b, are agonists in the complement system. These relationships are shown in the diagram depicted in FIG. 1.

The complement system is a blessing when it operates as intended, but it has to be kept under control because it can mark the body's own tissues for destruction. Thus, humans and other animals provide mechanisms whereby various components of the complement system which behave in this agonistic fashion can be destroyed, especially when associated with cells which are endogenous to the host.

There are two general mechanisms for this inhibition of the effects of the complement system. The first mechanism is generally reversible, facilitating the dissociation of the C3 convertases—i.e., C3b from Bb and C4b from C2a. Facilitation of dissociation is sometimes known as decay acceleration. The dissociation may also involve reversible binding of the antagonist proteins to C3b or C4b components, thus preventing their reassociation. The other mechanism, which is an irreversible inactivation process, results from proteolytic cleavage of the C3 convertase components C3b or C4b by the serine protease factor I. This proteolytic cleavage occurs only in the presence of a cofactor. Both general regulatory mechanisms, the facilitation of dissociation of C3b and C4b and the inactivation of C3b and C4b through cleavage by factor I, also apply to the inhibition of the alternative pathway C5 convertase (C3bBbC3b) and the classical pathway C5 convertase (C4bC2aC3b).

The proteins encoded by a region of the genome which is designated the "regulators of complement activation" (RCA) gene cluster are involved in both of the foregoing mechanisms. Currently, it is known that at least six proteins are encoded by this region. These are summarized in Table 1.

TABLE 1

RCA Proteins: Functional Profile

| Name | Primary Ligand(s) | Decay Acceleration (Dissociation) | Cofactor Activity |
|---|---|---|---|
| CR1 | C3b/C4b | + | + |
| MCP | C3b/C4b | – | + |
| DAF | C3b/C4b C3 Convertases | + | – |
| C4bp | C4b | + | + |
| Factor H | C3b | + | + |
| CR2 | C3dg | – | ? |

These proteins share certain structural similarities which will be further described below.

The reversible binding to C4b or C3b to dissociate the C3 convertases is effected by two plasma proteins designated C4 binding protein (C4bp) and factor H, and by two membrane proteins designated decay acceleration factor (DAF) and complement receptor 1 (CR1). Reversible binding to C4b is effected by C4bp, DAF and CR1 while reversible binding to C3b is effected by factor H, DAF and CR1.

The irreversible inactivation of the C3 convertases resulting from proteolytic cleavage of convertase components C3b or C4b by the enzyme factor I can occur by virtue of cofactor activity effected by the above-mentioned factor H and C4bp in the plasma and by CR1 and membrane cofactor protein (MCP) at the cell surface. Cofactor activity for cleavage of C3b is effected by factor H, CR1 and MCP while cofactor activity for cleavage of C4b is effected by C4bp, CR1 and MCP. It is also possible that the sixth protein, complement receptor 2 (CR2), has this cofactor activity at the cell surface.

Thus, for the six proteins encoded by the RCA gene cluster, factor H, C4bp, and CR1 have both reversible dissociation activity and irreversible cofactor activity; DAF has only reversible dissociation activity, and MCP and possibly CR2 have only irreversible cofactor activities. CR1, DAF and MCP interact with both C3b and C4b; C4bp interacts primarily with C4b, and factor H interacts primarily with C3b.

The Hourcade article referenced and incorporated above describes the relationship of these proteins as judged by comparison of deduced amino acid sequences from cDNAs. The cDNAs corresponding to CR1, CR2, DAF, MCP, C4bp, and factor H have all been obtained and sequenced. Evaluation of these comparative sequences has lead to the alignment set forth in FIG. 1 which shows the organization of the RCA proteins into SCR-containing and non-SCR-containing regions with the N-terminal ends at the left. In this figure, TM refers to transmembrane domain, C to cytoplasmic domain, O to O-linked glycosylation domain, G to glycolipid anchor, U to domain with unknown significance and D to a disulfide bridge-containing domain.

It is seen that there is considerable uniformity across the RCA family of proteins. All of them are composed of 60–70 amino acid repeating units commonly designated "short consensus repeats" (SCRs). Each SCR shares a number of invariant or highly conserved amino acid residues with other SCRs in the same protein or SCRs in other family members. Those members of the family which are membrane bound also have, at their C-termini, transmembrane regions and intracellular regions or else they have a glycolipid anchor.

The SCRs form the extracellular portions of those members of the family which are membrane-bound and almost all of the protein structure in the secreted members. Two covalently-crosslinked cysteine pairs establish two loops within each SCR. The smallest family members are DAF and MCP; each contains 4 SCRs followed by an O-linked glycosylation region. DAF is terminated with a glycolipid anchor while MCP ends with an extracytoplasmic segment of unknown significance, a transmembrane region and an intracellular domain. Of the secreted members of the family, factor H contains 20 SCRs, while the native form of C4bp is an association of seven subunits of 8 SCRs (the C4bp alpha chains) and one subunit of 3 SCRs (the C4bp beta chain). Both C4bp chains conclude with non-SCR domains that interconnect the chains through disulfide linkages. CR2 contains 16 SCRs, a transmembrane region and an intracellular domain. CR1 contains 4 repeating units of 7 similar SCRs (long homologous repeats or LHRs) numbered 1–28 followed by an additional 2 SCRs designated 29 and 30, a transmembrane region and an intracellular region.

Klickstein, L. B., et al., *J Exp Med* (1988) 168:1699–1717, described the identification of distinct C3b and C4b recognition sites in CR1 using deletion mutagenesis. They concluded that a single primary C4b binding site is located in SCR 1–2, while two major C3b binding sites are located in SCR 8–9 and SCR 15–16. C3b cofactor activity was localized to SCR 8–9 and SCR 15–16.

Hourcade, D., et al., *J Exp Med* (1988) 168:1255–1270, described a cDNA clone designated CR1-4 that encodes the first 8 and one-half amino terminal SCRs of CR1. This cDNA was transfected into COS cells and this resulted in the synthesis of a secreted truncated form of CR1 with a molecular weight of 78 kd (Krych et al., 1991). This shortened form of the protein, as shown hereinbelow, binds mainly C4b.

The multiple binding sites of CR1 can cooperate in their interactions with C3b-containing targets. In vitro, CR1 binds C3b—C3b dimers much more tightly than C3b monomers because binding to dimers can occur simultaneously at two sites in the same CR1 molecule (Wong and Farrell *J Immunol* (1991) 146:656; Ross and Medof *Adv Immunol* (1985) 37:217). Deletion of one of the two primary C3b binding sites can reduce the binding of CR1 to C3b—C3b by a factor of 10 (Wong and Farrell *J Immunol* (1991) 146:656.) It is likely that the primary C4b binding site also cooperates with the primary C3b-binding sites in interactions with targets that contain both C3b and C4b. These effects have an important consequence in vivo: CR1 has a higher affinity for targets densely coated with C3b and with targets densely coated with C3b plus C4b.

In addition, the C5 convertases, which are important in the stimulation of inflammation and in lysis of some target cells, are composed of multiple CR1 ligands: The classical C5 convertase contains C3b and C4b (C4bC3bC2a) while the alternative pathway C5 convertase contains two C3b proteins (C3bC3bBb). Inactivation of the C5 convertases by CR1 can also involve cooperation between more than one CR1 binding site. Indeed, it has been shown (Wong and Farrell *J Immunol* (1991) 146:656) that more than one CR1 C3b binding site may be essential for effective inhibition of alternative pathway C3 and C5 convertases.

It is recognized that the proteins encoded by the RCA gene cluster could be prepared recombinantly and used in diagnosis and therapy for the regulation of the complement system. The problems of transplantation of xenografts were reviewed by Platt, J. L., et al., in *Immunology Today* (1990) 11:450–457. Evidence has accumulated that the immediate hyperacute rejection of discordant xenografts is caused by recipient complement activity. Transgenic animals expressing human complement regulators (such as DAF or MCP) on cell surfaces could be an abundant source of organs that would be protected form hyperacute rejection in human recipients. A soluble complement inhibitor could also play a role in protecting xenografts from complement-mediated rejection.

The ability of a recombinant soluble form of CR1 to inhibit inflammation in the reversed passive Arthus reaction in rats was described by Yeh, C. G., et al., *J Immunol* (1991) 146:250–256. This soluble CR1 was obtained in Chinese hamster ovary (CHO) cells from expression of a CR1 genetic construct which had been mutated to remove the transmembrane and cytoplasmic domains. The ability of a similar soluble CR1, produced also recombinantly in CHO cells, to inhibit post-ischemic myocardial inflammation and necrosis in rats was reported by Weissman, H. F., et al., *Science* (1990) 249:146–151.

Proteins related to the RCA proteins have also been shown to be produced by viruses, presumably as a mechanism whereby infection by the virus can be facilitated (Kotwaal, J., et al., *Nature* (1988) 335:176–178; McNearney, T. A., *J Exp Med* (1987) 166:1525–1535).

Complete inhibition of the complement system on a long-term basis is not likely to be desirable in most individuals. In some cases of autoimmune disease, inhibition of the classical pathway alone may be sufficient. In the case of the xenograft, however, stringent inhibition of both pathways may be important. Similar stringency may be required for other applications. Accordingly, alternative modulators of the complement system with regulatable binding activities would be desirable. The present invention provides a means to prepare modified forms of RCA-encoded proteins with altered binding specificities and affinities which permit closely controlled modulation of the complement system.

DISCLOSURE OF THE INVENTION

The invention is directed to analogs of RCA-encoded proteins which analogs are modified full-length or truncated forms of these regulatory proteins. These analogs also include modifications of RCA hybrids, which can contain one or more SCRs from more than one RCA protein, and modifications of RCA recombinants in which SCRs are arranged in new orders. The modifications reside in the adjustment of the binding specificity and affinity of the analog as compared to the protein including the truncated, hybrid or recombined form thereof from which the modification was taken. These analogs are useful in controlling the complement system, and thus may be useful in the treatment of autoimmune diseases, the suppression of rejection of transplants, in diagnosis and the reduction in tissue damage associated with myocardial infarctions and cerebral vascular accidents. They may also play a role in the diagnosis of conditions associated with complement activation and immune complex formation.

Thus, in one aspect, the invention is directed to analogs of RCA-encoded proteins including their truncated, hybrid, and recombined forms, which analogs have different binding specificities and/or affinities from the unmodified protein. In another aspect, the invention is directed to recombinant materials useful in the production of these analogs. In still another aspect, the invention is directed to pharmaceutical compositions wherein these analogs are active ingredients and to methods of diagnosis using these analogs. In still another aspect the invention is directed to methods of preparing the analogs of the invention.

BRIEF DESCRIPTION OF THE DRAWINGS

FIG. 2A. A representation of the short consensus repeat is shown with highly conserved residues indicated. FIG. 2B. SCR organization of the RCA proteins (SEQ ID NO:14).

Figure 3:
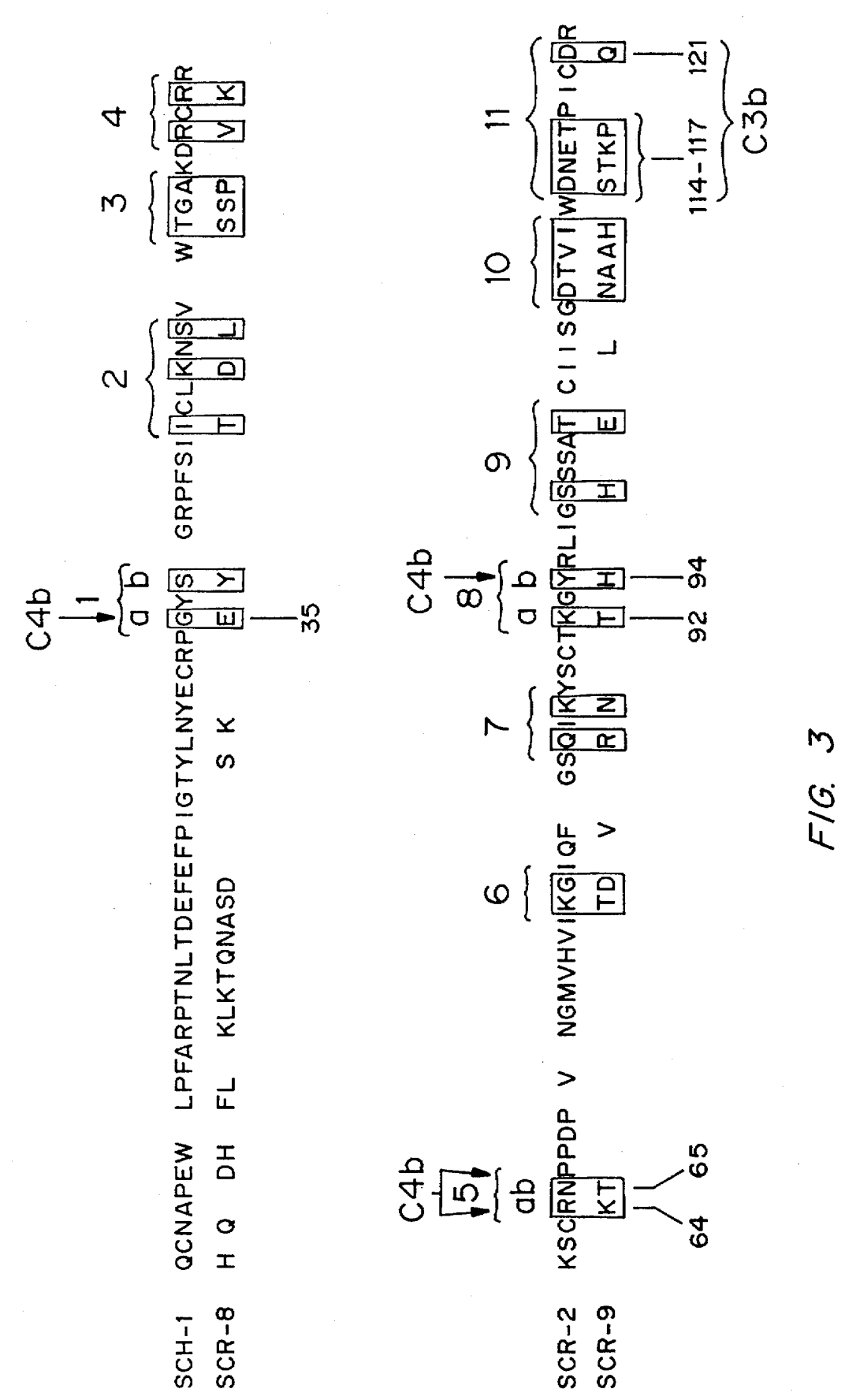

FIG. 3 shows representations of the amino acid sequences of SCR-1, SCR-2, SCR-8 and SCR-9 of full-length CR1. The full amino acid sequences of SCR-1, SCR-2, SCR-8 and SCR-9 are set forth respectively in SEQ ID NO:10, SEQ ID NO:12, SEQ ID NO:11 and SEQ ID NO:13. The amino acid sequences of SCR 15–16 are identical to those of SCR 8–9 excepting the presence of a T at position 110. The enumeration is consistent with that of Hourcade et al., *J Exp Med* (1988) 168:1255–1270, with the first amino acid (Q) of the mature receptor designated as amino acid #1. The corresponding position in CR1 SCR 8 is similarly designated. (SEQ ID NO:10), (SEQ ID NO:11), (SEQ ID NO;12), (SEQ ID NO:13).

MODES OF CARRYING OUT THE INVENTION

The invention provides a family of RCA protein analogs which can be used to modulate the complement system to adjust its activity in the face of various biological situations. The ability, provided by the invention herein, to adjust the binding specificity of the members of this protein family in both membrane-bound and soluble forms, permits the modulation to be adjusted to accommodate either long-term or short-term needs with respect to regulating the complement system, as well as affecting its activity by adjusting the balance between the classical and alternative pathways. Identification of the C4b and C3b binding sites in CR1, combined with the knowledge of the corresponding sequences genetically coded into the remaining members of the RCA family permits production of a wide range of analogs with predetermined specificity and affinity.

Figure 1:
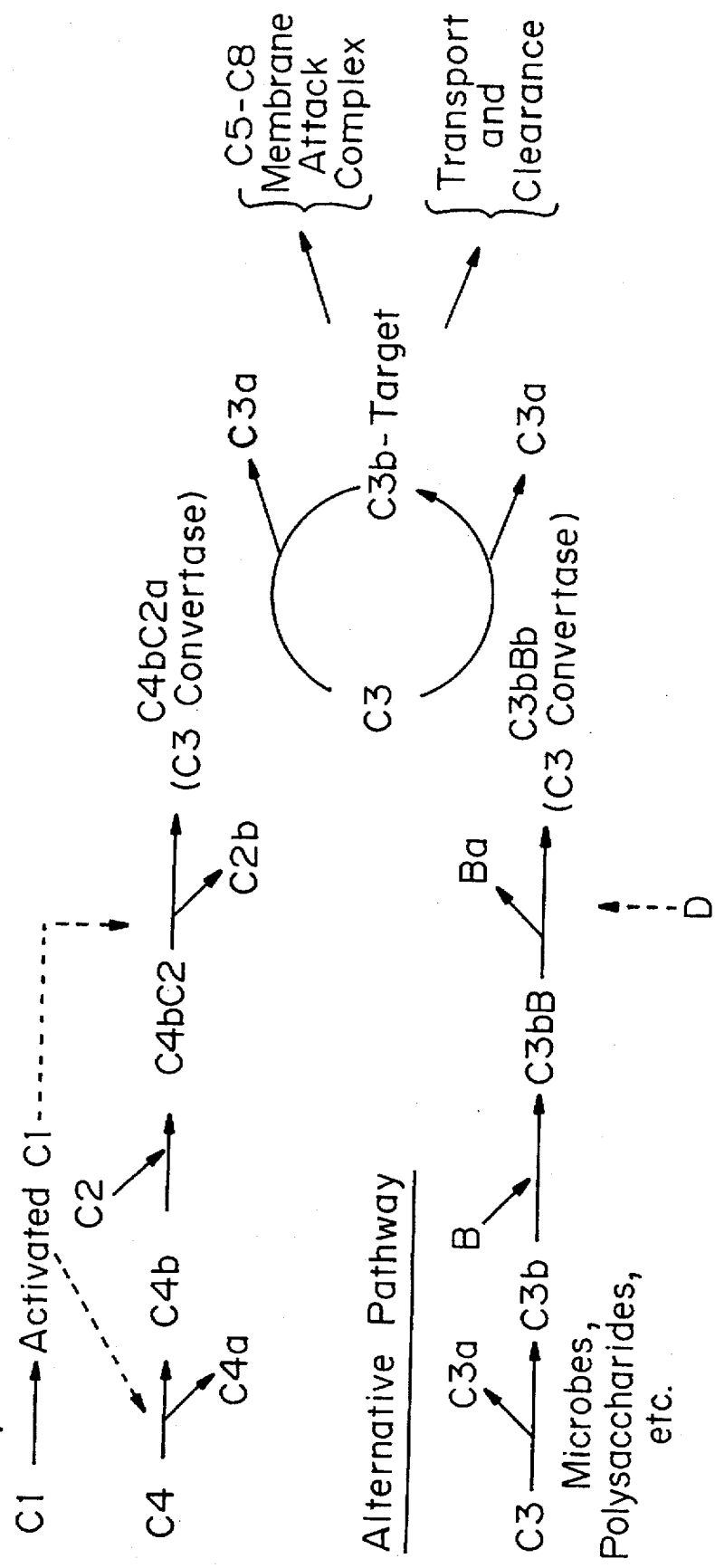
FIG. 1 is a schematic of the classical pathway for complement activation as described in the prior art

The identification of the amino acid sequences essential (or refractory) to binding to C4b and C3b permits transposition of similar sequences into corresponding regions of the same protein or corresponding regions of other family members or alteration of sequences which bind these proteins so as to alter their affinities. Corresponding regions can be identified by degree of amino acid sequence homology. In the case of CR1, four corresponding regions of interest are SCR 1–2, SCR 8–9, SCR 15–16 and SCR 22–23. The SCR portions labeled 2–3 in FIG. 1 for DAF correspond to those labeled 1–2, 8–9, 15–16 and 22–23 in CR1. Substitution of portions of DAF with homologous CR1 sequences provide forms of DAF with cofactor activity and/or binding activity, such as is exhibited by CR1. Similarly, substitutions of portions of MCP with homologous sequences could provide forms of MCP with increased binding affinity and cofactor activity and/or increased dissociation activity. Similarly, it may be possible to design a more potent soluble complement inhibitor by modifying corresponding regions to increase affinity for C4b and C3b or to design soluble complement inhibitors that specifically inhibit one part of the complement system.

In addition, substitution of amino acids that alter C3b or C4b binding could be made to noncorresponding SCRs of CR1 or other RCA proteins, including the truncated, hybrid and recombined forms thereof. In such cases, specific amino acids can be selected for replacement based on their positions with respect to highly conserved amino acids found in characteristic positions in all or most SCRs. In this manner, for example, binding sites could be added to SCRs not normally contributing directly to binding capacity.

As used herein, "RCA proteins" refers to proteins encoded by the gene cluster at the genetic region 1q32, which encodes six known proteins effective in complement regulation, factor H, C4bp, CR1, CR2, DAF and MCP. In addition, an apparent coding region similar to the amino terminal coding region of the CR1 gene has been located in this cluster, although it is unclear whether this sequence is expressed (Hourcade, D., et al., *J Biol Chem* (1990) 265:974–980). The term "RCA proteins" also refers to a group of proteins which are comprised of short consensus repeats (SCR) which can be identified as homologous across members of this family. "RCA proteins" also include truncated, hybrid and recombined forms of the RCA proteins. "Truncated" forms are simply shorter versions of the RCA proteins, typically modified so as to remove the C-terminal regions which effect membrane binding or secretion and sometimes modified further by deletion of one or more SCRs. "Hybrid" forms are RCA proteins that are composed of portions, i.e., the SCRs, of one RCA protein combined with SCRs of one or more other RCA proteins. "Recombined" forms are those wherein the SCRs of an RCA protein are rearranged in a new order. Of course, "RCA protein" also includes proteins which result from combinations of these changes.

The "analogs" of the invention are the above-defined RCA proteins, including truncated, hybrid, and recombined forms which have been specifically modified by alterations in the amino acid sequences associated with C3b and C4b binding sites.

In some preferred embodiments, these modifications are made by using corresponding SCRs of the protein as sites for alteration. By "corresponding SCR" is meant the most highly homologous SCR as judged by the amino acid sequences of the protein. Exon structure can in some cases facilitate this assignment. Thus, as set forth above, SCRs 1–2 of CR1 correspond to SCRs 2–3 of DAF; in addition, it is known that SCRs 1–2 of factor H, CR1, C4bp and MCP are corresponding sequences among these proteins. As noted above, CR1 is organized into a series of long homologous repeats (LHRs) containing 7 SCRs so that CR1 SCRs 1–7 correspond to CR1 SCRs 8–14; 15–21; and 22–28. CR2 is organized into a series of long homologous repeats of 4 SCRs in length. SCR 1–2 of CR1 corresponds to SCR 3–4, SCR 7–8, SCR 11–12 and SCR 15–16 of CR2.

In other preferred embodiments, the modifications are made by reference to highly conserved amino acids found in characteristic positions in all or most SCRs, as further illustrated in the examples below.

Either of the above strategies can be used to determine "corresponding positions" in the same or different RCA protein.

As shown hereinbelow, the C3b binding sequence in CR1, S-T-K-P-P-I-C-Q (SEQ ID NO:1), can be transferred to corresponding locations or to locations referenced to conserved amino acids in alternative SCRs to confer C3b binding. Conversely, the homologous sequence in SCR-2 of CR1, i.e., D-N-E-T-P-I-C-D (SEQ ID NO:2), can be transferred by substitution to such locations in C3b-binding SCRs in order to decrease C3b binding. In addition, the C4b binding regions are shown to be associated with three separate critical locations in SCR-1 and SCR-2 of CR1 in the proximity of amino acids 35, 64–65, and 92–94. Alterations in amino acid sequences of the corresponding SCRs in CR1 or in additional RCA family members or their truncated, hybrid, or recombined forms in these positions thus result in alterations in C4b binding activity.

In addition, structurally similar amino acids can substitute in such transfers for some of the specified amino acids. Groups of structurally similar amino acids include: (I,L,V); (F,Y); (K,R); (Q,N); (D,E); and (G,A).

Preparation of the Invention Analogs

The analogs of the invention are most conveniently prepared using recombinant techniques. The genes encoding the various members of the RCA protein family are of known sequence and are published. cDNA corresponding to CR1 has been described by Klickstein, L. B., et al., *J Exp Med* (1987) 165:1095, Klickstein, L. B., et al., *J Exp Med* (1988) 168:1699; Hourcade, D., et al., *J Exp Med* (1988) 168:1255. The cDNA encoding CR2 has been described by Moore, M. D., et al., *Proc Natl Acad Sci USA* (1987) 84:9194, and by Weiss, J. J., et al., *J Exp Med* (1988) 167:1047. The cDNA encoding DAF has been described by Caras, I. W., et al., *Nature* (1987) 325:545, and by Medof, M. E., et al., *Proc Natl Acad Sci USA* (1987) 84:2007. The cDNA encoding MCP has been described by Lublin, D. M., et al., *J Exp Med* (1988) 168:181, that for C4bp alpha chain by Chung, L. P, et al., *Biochem J* (1985) 230:133, and that for C4bp beta chain by Hillarp, A., and Dahlback, B., *Proc Natl Acad Sci USA* (1990) 87:1183; factor H encoding cDNA has been described by Ripoche, J., et al., *Biochem J* (1988) 249:593.

As the cDNAs encoding these proteins are known and the amino acid sequences have been deduced, comparison of corresponding regions of the various proteins of the member families is possible. In addition, the availability of the cDNA sequence makes possible the preparation of genetic constructs encoding truncated forms and the analogs of the invention using standard site-directed mutagenesis techniques, such as those described by Kunkel, T. A., et al., *Methods Enzymol* (1987) 154:367–382. Preparation of the analogs thus involves as a first step identification of the corresponding region of the target protein through sequence homology and site-directed mutagenesis in this region to alter C4b or C3b binding properties.

After the gene encoding the analog is prepared, expression can be obtained using standard recombinant techniques as is by now well known in the art. The gene sequence is ligated into suitable expression vectors under the control of sequences known to be appropriate to the desired host. Production of recombinant proteins in microbial systems such as *E. coli, B. subtilis,* various strains of yeasts, and other fungi, such as Aspergillus, is well known. It may be advantageous to produce the desired analogs in cells of higher organisms as well, such as the standard BPV/C127 system, the Baculovirus/insect cell system, CHO cells, COS cells, and other mammalian cells or in transgenic animals. Standard expression systems in various cell lines are by now well known and standard in the art. Transgenic animals can be constructed for several species. Production in transgenic animals is important in the context of preparing transplants for use in other species.

The analogs recombinantly produced in culture can be purified from the cell culture using standard purification techniques such as chromatography, for example ion-exchange chromatography, electrophoresis, and the like.

While recombinant production of the analogs of the invention is clearly the most convenient and practical method, it may also be possible directly to synthesize the analogs using protein synthesis techniques, such as standard solid-phase peptide synthesis technology. This approach may be suitable in particular in the case of truncated forms of the RCA protein family having modified amino acid sequences as analogs of the invention.

Assay Systems

The analogs of the invention can be verified to have the desired biological activities among those characteristic of the RCA family using in vitro or in vivo assays. In vitro systems such as those described by Wong and Farrell (*J Immunol* (1991) 146:656) can be used to measure effects on the complement pathways. In vivo and general biological effects can be assessed as described by Weisman, et al. (*Science* (1990) 249:146); or Yeh, et al. (*J Immunol* (1991) 146:250). The most potent analogs based on these criteria are candidates for therapeutic agents.

Utility and Administration

The analogs of the invention which are capable of binding C3b and/or C4b are useful as diagnostic tools in assessing the presence, absence or amount of C3b or C4b or C3b/C4b-bearing immune complexes in biological fluids. Such assays take advantage of the ability of the analog specifically to bind C3b and/or C4b and can be conducted in a variety of formats as is generally known. Formats for specific binding partner assays include direct and competitive formats, sandwich assays, agglutination assays and the like. Complexation between members of the specific binding pair can be conducted in solution or on a solid phase and can be detected using a variety of labeling techniques including fluorescence, radioisotopes, chromophores, and visible particles.

Typical reagent kits useful in assays for C3b and/or C4b and/or C3b/C4b-bearing immune complexes would include the analog specifically binding to the analyte optionally coupled to a solid support and additional labeling reagents useful in the assay. For example, one of many formats for the assay might include treating the sample to be tested with a solid support to which is coupled the analog of the invention as a "capture" specific binding partner, washing the support which has been treated with sample suspected of containing analyte, and then treating the washed support with anti-C3b or anti-C4b antibody labeled with an enzyme such as horseradish peroxidase. The presence of labeled enzyme on a support then is detected by addition of a substrate solution which results in the development of a color in the presence of the enzyme. The foregoing is, of course, merely illustrative and dozens of possible protocols could be designed which employ and take advantage of the specific binding properties of the analogs of the invention for C3b and/or C4b.

The analogs of the invention are also useful in therapeutic and prophylactic contexts. Complement activation can account for substantial tissue damage in a wide variety of autoimmune/immune complex mediated syndromes such as systemic lupus erythematosus, rheumatoid arthritis, hemolytic anemias, myasthenia gravis and others. Inhibition of the complement system is likely to be desirable therapeutic intervention in these cases. In some instances, specific inhibition of the classical pathway alone by RCA analogs could be preferred since long-term inhibition of the alternative pathway could lead to grave side effects.

Inhibition of complement activation could also be desirable in cases that involve tissue damage brought about by vascular injury such as myocardial infarction, cerebral vascular accidents or acute shock lung syndrome. In these cases, the complement system may contribute to the destruction of partially damaged tissue as in reperfusion injury. Highly stringent inhibition of complement for relatively brief periods might be preferred in these instances and soluble RCA analogs designed for higher potency may prove especially useful.

Complement inhibition may also prove important in the prevention of xenograft rejection. It is possible that organs derived from animals transgenic for human DAF or MCP may be protected from complement-mediated hyperacute rejection by the expression of transgenic DAF or MCP on the cell surfaces of the xenograft. Animals transgenic for RCA analogs designed for higher potency may provide more successful xenografts. Soluble RCA analogs may also prove useful in protecting the transplant in the recipient. Thus, there are many situations that call for inhibition of complement. The ability to modify RCA proteins, and their truncated, recombined and hybrid forms allows the design of therapeutic agents appropriate to each case.

The dosage level and mode of administration of the analogs of the invention depend on the nature of the analog, the nature of the condition to be treated, and the history of the individual patient. Systemic administration is generally required which may be by injection or by transmucosal or transdermal delivery. Administration by injection may be intravenous, intramuscular, intraperitoneal or subcutaneous. Formulations for injection are generally biocompatible solutions of the active ingredient such as Hank's solution or Ringer's solution. Formulations for transdermal or transmucosal administration generally include penetrants such as fusidic acid or bile salts in combination with detergents or surface-active agents. The formulations can then be manufactured as aerosols, suppositories, or patches.

Oral administration is generally not favored for protein or peptide active ingredients; however, if suitably formulated so as to be protected from the digestive enzymes, oral administration can also be employed. Suitable formulations for a desired mode of administration can be found in *Remington's Pharmaceutical Sciences*, latest edition, Mack Publishing Co., Easton, Pa. The dosage levels and precise formulations are obtainable by routine optimization procedures as is generally known in the art.

The following examples are intended to illustrate but not to limit the invention.

EXAMPLE 1

Binding Specificity of Truncated CR1

The cDNA clone CR1–4 described hereinabove which encodes the first 543 amino acids of mature CR1 (SCR 1–8 and ½ of SCR-9) was transfected into COS cells to obtain a secreted protein designated CR1–4.

Two mouse monoclonal anti-CR1 antibodies were used to determine the immunoreactivity of CR1–4, and as a method to assay for this protein. Antibody E11 (Hogg, N., et al., *Eur J Immunol* (1984) 14:236–243), and 3D9 (O'Shea, J. J., et al., *J Immunol* (1985) 134:2580–2587), recognized CR1 and bound to the recombinantly produced CR1–4.

Binding to C4b or to C3b was tested using either C4b or iC3 (C3 containing a broken thioester bond analogous in reactivity and function to C3b) bound to a Sepharose support as described by Dykman, T., et al., *Proc Natl Acad Sci USA* (1983) 80:1698–1702, and Cole, J. L., et al., *Proc Natl Acad Sci USA* (1985) 82:859–863. Binding to these solid-supported substrates was verified by testing by an ELISA for CR1. The C4b derivatized support was able to bind CR1–4 and the binding was shown to be ionic strength-dependent in a manner similar to that known for CR1. Most efficient binding occurred at Furthermore, solubilized C4b inhibited binding of the protein to C4b-derivatized support but soluble iC3 did not inhibit this binding. This confirms that CR1–4 binds primarily C4b but not iC3 (C3b).

EXAMPLE 2

Construction of CR1–4 Analogs

Figure 2A:
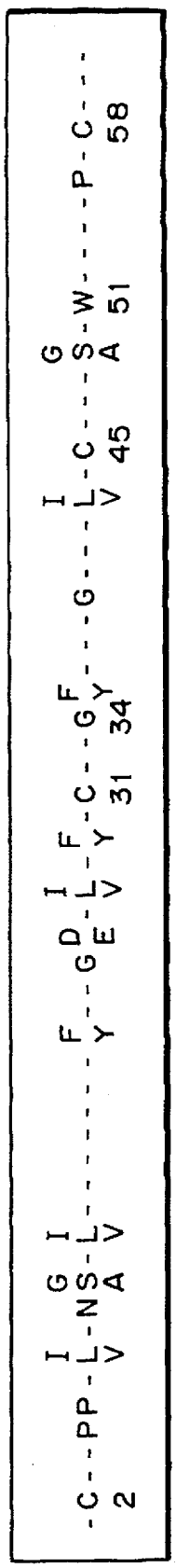
FIGS. 2A and 2B shows schematically the structures and relationships of RCA-encoded proteins.
Figure 2B:
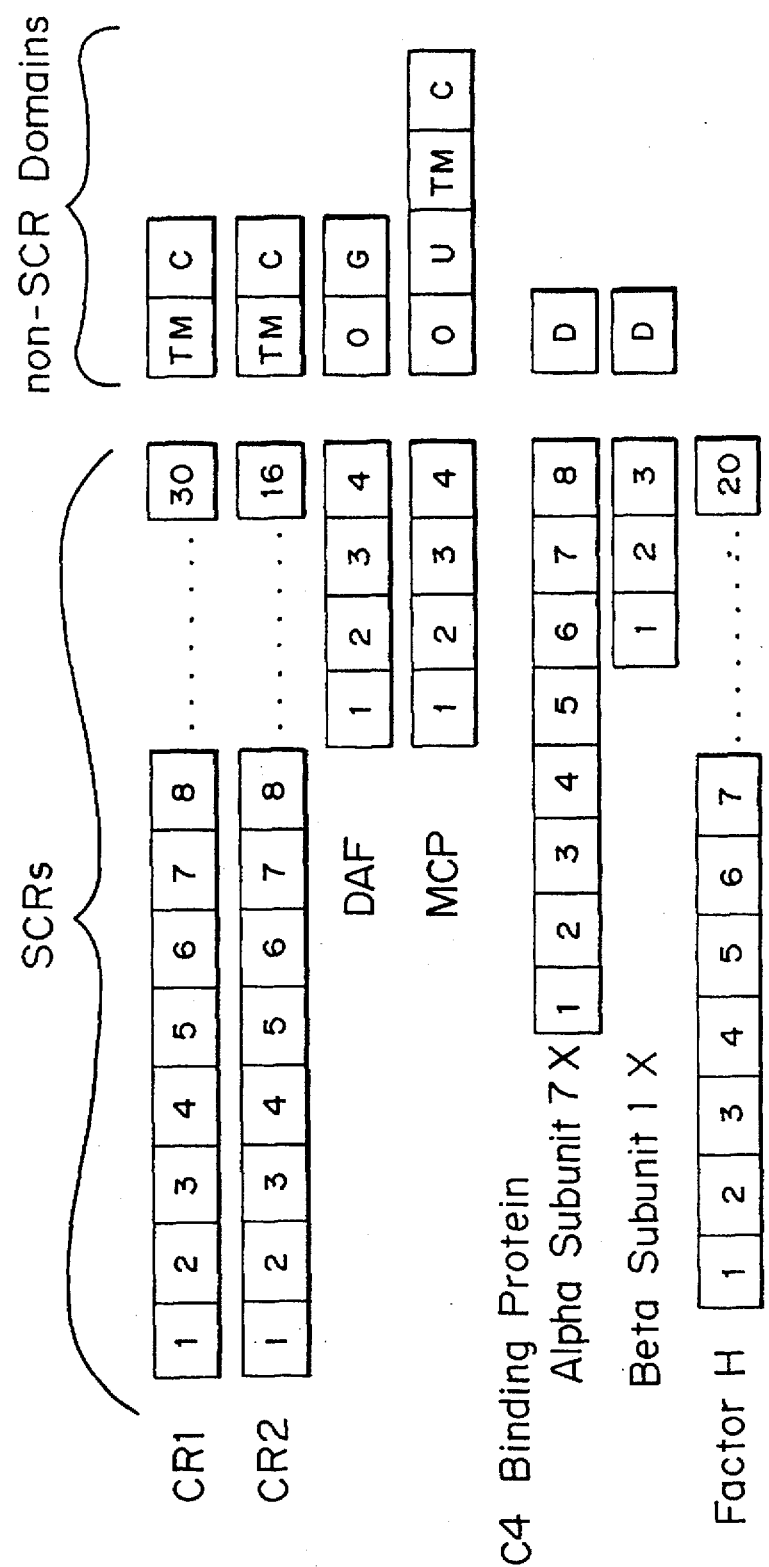

Various mutated forms of CR1–4 were constructed and tested for binding activity to C4b and iC3 as described above in Example 1. Table 2 shows the analogs constructed and the effects on binding obtained. In Table 2, the modifications are shown by the number of the amino acid and the conversion effected. The numbers correspond to those set forth in FIG. 2 which sets forth the amino sequences of SCR-1, SCR-2, SCR-8 and SCR-9 in CR1.

TABLE 2

CR1–4 Mutants

| Designation | Description | C4b-binding | C3b-binding |
|---|---|---|---|
| CR1–4 | original peptide | + | – |
| ΔSCR-1 | amino acids 1–60 deleted | – | – |
| ΔSCR-2 | amino acids 61–122 deleted | – | – |
| 1 | 35:G→E; 37:S→Y | – | – |
| 1a | 35:G→E | – | – |
| 1b | 37:S→Y | + | – |
| 2 | 44,47,49:I . . . K . . . S→T . . . D . . . L | + | – |
| 3 | 52–54:T—G—A→S—S—P | + | – |
| 4 | 57,59:R . . . R→V . . . K | + | – |
| 5 | 64,65:R—N→K—T | +/– | – |
| 5a | 64:R→K | +/– | – |
| 5b | 65:N→T | +/– | – |
| 6 | 78,79:K—G→T—D | + | – |
| 7 | 85,87:Q . . . K→R . . . N | + | – |
| 8 | 92,94:K . . . Y→T . . . H | – | – |
| 8a | 92:K—T | ++ | – |
| 8b | 94:Y→H | – | – |
| 9 | 99,103:S . . . T→H . . . E | + | – |
| 10 | 109–112:D—T—V—I (SEQ ID NO:15)→N—A—A—H (SEQ ID NO:16) | + | – |
| 11 | 114–117,121:D—N—E—T amino acids 54–57 of SEQ ID NO:12) . . . D→S—T—K—P (amino acids 54–57 of SEQ ID NO:13) . . . Q | + | + |
| 11a | 114:D→S | + | – |
| 11b | 115:N→T | + | – |
| 11c | 116:E→K | + | – |
| 11d | 117:T→P | + | – |
| 11c,d | 116,117:E—T→K—P | + | – |
| 11e | 121:D→Q | + | – |
| 11ΔSCR1 | 1–60 deleted, 114–117 121: D—N—E—T(amino acids 54–57 of SEQ ID NO:12) . . . D→S—T—K—P (amino acids 54–57 of SEQ ID NO:13) . . . Q | – | – |

As shown in Table 2, deletion of either SCR-1 or SCR-2 results in loss of C4b-binding activity; thus both regions are required for binding to C4b. Binding to C3b is conferred by insertion of the SCR-9 sequence S-T-K-P-(P-I-C)-Q (SEQ ID NO:1) into SCR-2; however, deletion of SCR-1 also eliminates binding to C3b in this mutant. Thus, binding to C3b requires not only the relevant sequence in SCR-2, but an additional portion of SCR-1. The ability to bind C3b conferred by altering the sequence in SCR-2 does not affect binding to C4b.

As Table 2 also shows, it is possible to weaken or destroy binding to C4b by altering amino acid 35, 64–65 or 94. It is possible to strengthen C4b binding by altering amino acid 92.

These results indicate that by manipulation of C3b and C4b binding sites in CR1 the affinity and specificity of CR1–4 can be altered. Similar alterations may be made to corresponding regions in additional members of the RCA protein family.

EXAMPLE 3

Soluble CR1 Analogs Which Specifically Inhibit the Classical Pathway

Soluble CR1 forms in general can be constructed by introducing a translational stop codon, in the correct reading frame, into the CR1 coding sequence of a CR1 construct. One example of this strategy was used by Weisman et al. (*Science* (1990) 249:146) in the construction of a CR1 form that is 30 SCRs in length, truncated at the alanine at position 1931, the first amino acid of the transmembrane segment of full length CR1. This soluble CR1 (herein referred to as sCR1) is illustrated as a starting material for the production of analogs, but many other sCR1 forms (for example, CR1–4 above) could also be used as starting material. This sCR1 form contains the C4b-binding region SCR 1–2, and the two identical C3b-binding regions, SCR 8–9 and SCR 15–16 (Klickstein et al., *J Exp Med* (1988) 168:1699). All three of these regions are corresponding sequences as previously defined. In addition, sCR1 contains a fourth corresponding region, SCR 22–23, for which there is no reported binding activity.

One family of sCR1 analogs has increased inhibition of the classical pathway by virtue of enhanced binding of C4b. Illustrative modifications that increase C4b binding include:

1. The affinity of the primary C4b active site in SCR 1–2 is increased by replacing K at position 92 by T. This enhances the C4b coenzyme functions and dissociation functions in that region.
2. The affinity of other corresponding regions of CR1 to C4b are increased by modifying positions in other SCRs corresponding to CR1 positions 35, 64, 65, 92 and 94 to include G (or structurally similar A), R, N (or Q), T, and Y (or F), respectively; preferably G, R, N, T, and Y, respectively. This, too, could increase the use of the primary C4b active sites in SCR 1–2, and establishes C4b coenzyme function or dissociation function at those corresponding regions.

As shown in Table 2, replacement of any of 5 specific amino acids of SCR 1–2 of CR1–4 with the corresponding amino acids of SCR 8–9 modifies C4b-binding capacity of CR1–4. Replacement of G at position 35 with E, or replacement of Y at position 94 with H abolishes detectable C4b binding. Replacement of R at position 64 with K and/or replacement of N at position 65 with T results in lower detectable C4b binding. Replacement of K at position 92 with T appears to increase C4b binding Using the above information, modifications are made for any or all four of the CR1 corresponding regions discussed above that lead to higher inhibition of the classical pathway as follows: SCR 1–2, the primary C4b-binding site of CR1, is modified by replacement of K at position 92 with T as in CR1–4 mutant #8a. SCR 8–9 and the identical SCR 15–16 are modified by reversing the replacements that decreased C4b-binding of CR1–4. Thus, modification of SCR 8–9 and SCR 15–16 is effected by the replacement of E at positions corresponding to 35 with G, H at positions corresponding to 94 with Y (or F), K at positions corresponding to 64 with R and T at positions corresponding to 65 with N (or Q). Using these same principles, SCR 22–23 is modified by replacement of G (or A) at the position corresponding to 64 with R, P at the position corresponding to 65 with N (or Q), E at the position corresponding to 92 with T and F at the position corresponding to 94 with Y.

Since the three regions corresponding to SCR 1–2 are highly homologous in amino acid sequence to SCR 1–2, and since two of them, SCR 8–9 and SCR 15–16 already have low levels of C4b binding activity detectable under certain conditions, substitution of one or more of those 4 amino acids found to be important for C4b-binding in SCR 1–2 into the corresponding positions in SCR 8–9, SCR 15–16, and SCR 22–23 facilitates the C4b-binding capacity of all three corresponding regions. These substitutions result in higher affinity of sCR1 for C4b, and result in the establishment of new coenzyme or dissociation functions or improvement in the capacity of the coenzyme and dissociation functions present on the sCR1 starting material.

In a second family of CR1 analogs that are specific inhibitors of the classical pathway, the capacity of CR1 to inhibit the alternative pathway is decreased. Wong and Farell (*J Immunol* (1991) 146:656) showed that at least two C3b binding sites were necessary for efficient in vitro inhibition of the alternative pathway convertases while only one C3b binding site was needed for the efficient in vitro inhibition of the classical pathway.

As shown in Example 2, substitution of a short stretch of amino acids in SCR 1–2 of CR1–4 with corresponding amino acids of SCR 8–9, specifically, replacement of D-N-E-T (Amino Acids 54–57 of SEQ ID NO:12) from positions 114–117 with S-T-K-P (Amino Acids 54–57 of SEQ ID NO:13) and replacement of D at position 121 with Q, confers C3b binding capacity to CR1–4. Replacement of any of these amino acids singly or E-T with K-P do not result in detectable increase in C3b binding. None of these substitutions results in detectable changes in C4b binding. Since positions 118–120 are P-I-C in both SCR 1–2 and SCR 8–9, it is believed that the entire amino acid sequence S-T-K-P-P-I-C-Q (SEQ ID NO:1) is essential for the observed increase in C3b binding.

Modification of one of the two primary C3b-binding sites reduces inhibition of the alternative pathway markedly without substantial effects on inhibition of the classical pathway (Wong and Farrell, *J Immunol* (1991) 146:656). Specifically, S-T-K-P-P-I-C-Q (SEQ ID NO:1) at positions corresponding to 114–121 in SCR 15–16 or SCR 8–9 in sCR1 is replaced with D-N-E-T-P-I-C-D (SEQ ID NO:2), to reduce C3b-binding capacity. Some structurally similar amino acids may also be substituted in the D-N-E-T-P-I-C-D (SEQ ID NO:2) sequence. This results in a soluble CR1 analog with only one remaining strong C3b-binding site, and thus lower affinity for alternative pathway targets. Since C3b-binding appears necessary for coenzyme activity, such a modification also lowers C3b coenzyme capacity.

Thus, in the design of a classical pathway inhibitor, two general classes of substitutions are proposed: One class is designed to increase C4b activity and the other class to reduce C3b activity. To produce an effective and specific classical pathway inhibitor, some or all of the above substitutions are made.

EXAMPLE 4

A More Potent Soluble CR1 Analog

A stringent inhibitor of the complement system has applications where higher potency is required. In this example, the sCR1 sequence is used as starting material for a family of analogs of higher inhibitory capacity for both classical and alternative pathways. Other CR1 truncated, full-length, recombined or hybrid forms or CR1 could also be used.

As noted above, the sCR1 protein contains four corresponding regions of interest: SCR 1–2, SCR 8–9, SCR 15–16 and SCR 22–23. The primary C4b-binding site is within SCR 1–2 and the two primary C3b-binding sites are in SCR 8–9 and SCR 15–16. SCR 22–23 has no reported binding activity although it is highly homologous in amino acid sequence to the other three corresponding regions.

Substitutions already described in previous examples are introduced into the four corresponding regions of interest in order to increase the affinity of sCR1 for its C3b and C4b-containing targets. These modifications are designed to increase the use of existing coenzyme and dissociation functions and may establish new coenzyme and dissociation functions. The introduction of amino acid sequences significant to C3b-binding into the C4b binding region probably would not interfere substantially with C4b activities since such a substitution in CR1-4 did not detectably alter the C4b binding properties of CR1-4. The introduction of amino acids significant to C4b-binding into C3b-binding regions probably would not interfere substantially with C3b-binding activities since substantial C3b-binding occurs in CR1-4 mutant 11, in which many amino acids specific to SCR 1–2, including those significant in C4b binding, are already present.

Specific substitutions designed to increase affinity to C4b are those already referred to in Example 3: SCR 1–2, the primary C4b-binding site of CR1, can be modified by replacement of K at position 92 with T. SCR 8–9 and the identical SCR 15–16 can be modified by replacement of E at a position corresponding to 35 by G (or A), H at a position corresponding to 94 by Y (or F), K at a position corresponding to 64 by R and T at position corresponding to 65 by N (or Q). SCR 22–23 can be modified by replacement of G at a position corresponding to 64 by R (or K), P at a position corresponding to 65 with N (or Q), E at a position corresponding to 92 with T and F at a position corresponding to 94 with Y.

Together, these modifications result in higher affinity for C4b and may also result in the establishment of new coenzyme or dissociation functions or the improvement in the capacity of the coenzyme and dissociation functions present on the sCR1 starting material.

As described in previous examples, substitution of a short stretch of amino acids into SCR 1–2 of CR1-4 by corresponding amino acids of SCR 8–9 confers C3b binding capacity to CR1-4. Replacement of D-N-E-T-P-I-C-D (SEQ ID NO:2) at position 114–121 in sCR1 SCR 1–2 by S-T-K-P-P-I-C-Q (SEQ ID NO:1) increases the affinity of sCR1 for C3b. Further, replacement of D-K-K-A-P-I-C-D (SEQ ID NO:3) at position 114–121 in SCR 22–23 by S-T-K-P-P-I-C-Q (SEQ ID NO:1) also increases the affinity of sCR1 for C3b. Some structurally similar amino acids may also be substituted in the S-T-K-P-P-I-C-Q (SEQ ID NO:1) sequence.

A more potent complement inhibitor, in general, provides increased C4b-binding and increased C3b-binding. This is achieved by introducing all the modifications set forth above.

EXAMPLE 5

DAF Analogs

The membrane-bound complement regulator DAF facilitates the dissociation of C3b and C4b-containing convertases but does not bind C3b or C4b, nor does it serve as cofactor for factor I-mediated proteolytic inactivation of C3b or C4b. It would be desirable, under certain situations, to increase the complement regulatory activity of DAF or of truncated, recombined or hybrid forms of DAF.

Based on amino sequence homology, DAF SCR 2–3 corresponds to the CR1 active regions. Homology between DAF SCR 2–3 and CR1 SCR 1–2 is 40% while homology between DAF SCR 2–3 and CR1 SCR 8–9 is 39%. (There are several unmatched amino acids in these alignments, so the position numbers of DAF do not precisely match those of CR1.)

Replacement of S-D-P-L-P-E-C-R (SEQ ID NO:4) at DAF position 180–187 (using the enumeration in Lublin and Atkinson, Ann Rev Immunol (1989) 7:35–58) with S-T-K-P-P-I-C-Q (SEQ ID NO:1) increases the affinity of DAF for C3b. Replacement of S-D-P-L-P-E-C (SEQ ID NO:5) with S-T-K-P-P-I-C-Q (SEQ ID NO:1) leaves R at the end of this segment, since R is found in the corresponding positions of CR1 SCR 1–2 and CR1 SCR 8–9. Some structurally similar amino acids can be substituted in the S-T-K-P-P-I-C-Q (SEQ ID NO:1) sequence.

Replacement of P at DAF position 130 with R (or K), especially R, increases the affinity of DAF for C4b. All other amino acids found important in C4b interactions in CR1 are already present in DAF SCR 2–3.

These substitutions, by increasing the affinity of DAF for C3b and, possibly, C4b, enhance the respective inhibitory effects of DAF on complement activation. These analogs are useful, for example, in the suppression of xenograft rejection. Animal donors transgenic for such a DAF analog are used to supply organs for transplantation to human recipients.

EXAMPLE 6

Soluble MCP Analogs That Specifically Inhibit the Classical Pathway

The membrane-bound complement regulator MCP binds both C3b and C4b and serves as cofactor for the factor I-mediated inactivation of both C3b and C4b. It could be attractive as a soluble complement inhibitor, especially if it were reconstructed to have multiple binding sites as in sCR1. One embodiment is use of a longer MCP form consisting of two or more tandem repeats of MCP SCR 1–4 as starting material. Analogs of this extended MCP are classical pathway-specific. As generally described for sCR1 in Example 3, all or some MCP repeats are modified to enhance C4b binding, and all but one MCP repeat are modified to decrease C3b binding.

The MCP SCR 1–2 corresponds to CR1 SCR 1–2; thus, several amino acid substitutions proposed for modifications of SCR 8–9 from CR1 in Example 3 will contribute to a greater affinity of MCP for C4b: Replacement of P at MCP position 66 (as enumerated by Liszewski et al., Ann Rev Immunol (1991) 9:431) by R (or K), especially R; replacement of Y at MCP position 67 by N (or Q), especially N; replacement of E at MCP position 95 by T.

The SCR 8–9 amino acid sequence that confers C3b binding to CR1-4, S-T-K-P-P-I-C-Q (SEQ ID NO:1), is closely matched in the corresponding MCP positions 117–124 (S-G-K-P-P-I-C-E) (SEQ ID NO:6). Replacement of these MCP amino acids with those from SCR 1–2 (D-N-E-T-P-I-C-D) (SEQ ID NO:2) of CR1 reduces C3b binding at each MCP region modified. Some structurally similar amino acids can be substituted in the D-N-E-T-P-I-C-D (SEQ ID NO:2) sequence. Replacement of the G at MCP position 118 with T and replacement of the E at MCP position 124 with Q (or N) increases C3b binding.

One embodiment used as the starting material is a 16 SCR-long tandem repeat of MCP SCR 1–4 that terminates directly following the 16th SCR, thus comprising four corresponding long homologous repeats (LHRs). In the illustrative analog, all corresponding regions are enhanced as described above to increase C4b affinity, and all but the LHR second from the amino terminal end are modified to suppress C3b binding. The second LHR is modified to increase C3b binding. This analog is a specific classical pathway inhibitor.

EXAMPLE 7

Analogs of Factor H

Factor H is a plasma protein consisting solely of 20 SCRs. Factor H exhibits C3b binding and C3b cofactor and dissociation capacity but no apparent ability to inactivate or bind C4b. Since factor H has already evolved as a plasma protein, it could be advantageous to use it as the starting material for soluble RCA analogs. Although the active sites of factor H are not precisely known, a proteolytic fragment composed of the first 5.5 SCRs of factor H exhibits C3b-binding and cofactor activity (Alsenz et al., *Biochem J* (1984) 389).

To increase the affinity of factor H for C3b binding, S-T-K-P-P-I-C-Q (SEQ ID NO:1) is introduced into several of the SCRs, none bearing a close correspondence to CR1 SCR 8–9. In one embodiment, the first six SCRs are left unmodified, thus retaining the original active site(s), and the remaining fourteen SCRs are modified by substitution of the S-T-K-P-P-I-C-Q (SEQ ID NO:1) into the position(s) homologous to CR1. Some structurally similar amino acids can substitute in the S-T-K-P-P-I-C-Q (SEQ ID NO:1) sequence. Homologous positions are readily identified because the W that precedes this C3b binding segment is found in most SCRs (it is found in all factor H SCRs except SCR 10 and SCR 20) while the C within the C3b binding segment is found in all the known SCRs. While not all substitutions will necessarily confer added binding activity, since these factor H SCRs are less homologous to the CR1 SCR 1–2 and CR1 SCR 8–9 regions. However, at least some modified H SCRs gain C3b-binding capacity, resulting in a factor H analog with much higher affinity for C3b. As discussed above, higher affinity would lead to the greater use of the active sites already present in the first six H SCRs.

EXAMPLE 8

A CR1–4 Analog as a Potent Classical Pathway Inhibitor

CR1–4 protein is a secreted form of CR1 that is composed of the first 8½ N-terminal SCRs of the CR1 receptor (Hourcade et al., *J Exp Med* (1988) 168:1255; Krych et al. (1991) in press.) While no protein or messenger corresponding to CR1–4 has been isolated in vivo, the CR1–4 cDNA was isolated from a human promyelocytic cell line, and there is a suggestion that CR1–4 mRNA may also be produced by human B cells transformed by Epstein-Barr virus. It is therefore possible that the CR1–4 protein is produced in vivo by transformed cells as a defense against complement.

As CR1–4 may function in vivo, it may already be more suited to circulating in the plasma than the sCR1 of Example 3; for example, it could be more stable. CR1–4 lacks the primary sites that mediate C3b cofactor activity, and is thus a classical pathway-specific inhibitor. CR1–4 may thus be used as a starting material for modifications analogous to those set forth in Example 3.

C3b and/or C4b affinities can be increased as follows, using as a starting material either CR1–4 or CR1–4 which has been modified as described in Table 2 at positions 114–121 and/or position 92. Building a new binding site could create cooperative binding effects as those seen in sCR1 interactions (Wong, W. et al., *J Immunol* (1991) 146:656). SCR 5–6 has been shown as not important for C4b-binding (Klickstein et al., *J Exp Med* (1988) 168:1699), so modifications in this region do not interfere with the C4b capacity already inherent in CR1–4. Amino acid sequence comparisons (Klickstein et al., *J Exp Med* (1987) 165:1095; and intron/exon structure of the respective coding regions of the CR1 gene (Hourcade, D. et al., *J Biol Chem* (1990) 265:974) demonstrate substantial homology and evolutionary relatedness between SCR 5–6 and SCR 1–2, and SCR 8–9.

In modifying SCR 5–6 of CR1–4, both C4b and C3b affinities are increased. Replacement of D—D at position 318–319 (as enumerated by Hourcade et al., *J Exp Med* (1988) 168:1255–1270) with R-N (or K-N, R-Q or K-Q) could increase C4b affinity. It is believed necessary to retain the two prolines following R-N in SCR1–2, so that replacement of D-D-F-M (SEQ ID NO:17) with R-N-P-P (SEQ ID NO:18) is preferred. Replacement of E at position 347 with T and F at position 349 with Y also increases C4b affinity. SCR 5–6 is also modified by replacement of N-S-S-V-P-V-C-E (SEQ ID NO:7) at positions 369–376 with S-T-K-P-P-I-C-Q (SEQ ID NO:1) from CR1 SCR 8–9 to increase C3b affinity. Some structurally similar amino acids can substitute in the S-T-K-P-P-I-C-Q (SEQ ID NO:1) sequence.

---

We claim:

1. A method to modulate the complement system in an animal subject comprising administering to an animal in need of such modulation an effective amount of a pharmaceutical composition comprising a complement inhibitor, wherein the complement inhibitor is selected from the group consisting of
  (a) an analog of a protein selected from the group consisting of complement receptor 1 (CR1), complement receptor 2 (CR2), decay accelerating factor (DAF), membrane cofactor protein (MCP), C4 binding protein (C4bp), and factor H, and
  these complement regulating proteins wherein the carboxy terminus is removed to allow the protein to be secreted,
  wherein said protein analog contains defined amino acid substitutions in the short consensus repeats selected from the group consisting of
    the protein wherein amino acids corresponding to amino acids 114–121 of CR1 are modified in a short consensus repeat to comprise the amino acid sequence S-T-(K/R)-P-P-(I/L/V)-C-(Q/N) (SEQ ID NO:8);
    the protein wherein the amino acids corresponding to positions 114–121 of CR1 are modified to contain the sequence S-T-K-P-P-I-C-Q (SEQ ID NO: 1);
    the protein wherein amino acids corresponding to positions 114–121 of CR1 are modified in a short consensus repeat (SCR) to contain the sequence (D/E)-(N/Q)-(E/D)-T-P-(I/L/V)-C-(D/E) (SEQ ID NO:9);
    the protein wherein amino acids corresponding to amino acids 114–121 of CR1 comprise the sequence D-N-E-T-P-I-C-D (SEQ ID NO:2);
    the protein wherein an amino acid corresponding to an amino acid selected from the group consisting of 35, 64, 65, and 94 of CR1 is selected from the group consisting of (G/A) 35, (R/K) 64, (N/Q) 65, and (Y/F) 94;
    the protein wherein an amino acid corresponding to an amino acid selected from the group consisting of 35, 64, 65, and 94 of CR1 is selected from the group consisting of G35, R64, N65, and Y94;
    the protein wherein the amino acid corresponding to amino acid 92 of CR1 is T; and
    the protein wherein an amino acid selected from the group consisting of 35, 64, 65, 92 and 94 of CR1 is substituted by a different amino acid residue than the corresponding amino acid of the naturally occurring CR1; and
  (b) an analog of a protein wherein said protein analog is CR1–4 having a modification selected from the group consisting of
    amino acids 1–60 deleted;
    amino acids 61–122 deleted;
    35:G→E; 37:S→Y;
    35:G→E;
    37:S→Y;
    44, 47, 49:I . . . K . . . S→T . . . D . . . L;
    52–54:T-G-A→S-S-P;
    57, 59:R . . . R→V . . . K;
    64, 65:R-N→K-T;
    64:R→K;
    65:N→T;
    78, 79:K-C→T-D;
    85, 87:Q . . . K→R . . . N;
    92, 94:K . . . Y→T . . . H;
    94:Y→H;
    99, 103:S . . . T→H . . . E;
    109–112:D-T-V-I (SEQ ID NO: 15)→N-A-A-H (SEQ ID NO:16);
    114–117, 121:D-N-E-T . . . D (SEQ ID NO:2)→S-T-K-P . . . Q (SEQ ID NO:1);
    114:D→S;
    115:N→T;
    116:E→K;
    117:T→P;
    116, 117:E-T→K-P;
    121:D→Q; and
    1–60 deleted, 114–117, 121:D-N-E-T (amino acids 54–57 of SEQ ID NO:12) . . . D→S-T-K-P (amino acids 54–57 of SEQ ID NO:13) . . . Q.

2. The method of claim 1 wherein the analog has enhanced C3b binding and wherein amino acids 114–121 of CR1 are modified in at least one SCR to contain the sequence of S-T-(K/R)-P-P-(I/L/V)-C-(Q/N) (SEQ ID NO:8).

3. The method of claim 2 wherein said amino acids 114–121 of CR1 are modified to contain the sequence S-T-K-P-P-I-C-Q (SEQ ID NO:1).

4. The method of claim 1 wherein the analog has decreased C3b binding and wherein amino acids 114–121 of CR1 are modified in a short consensus repeat to contain the sequence (D/E)-(N/Q)-(E/D)-T-P-(I/L/V)-C-(D/E) (SEQ ID NO:9).

5. The method of claim 4 wherein said amino acids 114–121 of CR1 are modified to contain the sequence D-N-E-T-P-I-C-D (SEQ D NO:2).

6. The method of claim 1 wherein the analog has enhanced C4b binding and wherein an amino acid selected from the group consisting of 35, 64, 65, and 94 of CR1 is selected from the group consisting of (G/A)35, (R/K)64, (N/Q)65, and (Y/F)94.

7. The method of claim 6 wherein said amino acid selected from the group consisting of 35, 64, 65, and 94 of CR1 is selected from the group consisting of G35, R64, N65, and Y94.

8. The method of claim 1 wherein the analog has enhanced C4b binding and wherein amino acid 92 of CR1 is T.

9. The method of claim 1 wherein the analog has reduced C4b binding and wherein an amino acid selected from the group consisting of 35, 64, 65, 92 and 94 of CR1 is substituted by a different amino acid residue than the amino acid of the naturally occurring CR1.

10. The method of claim 1 wherein the analog is CR1-4 which is modified by a change selected from the group consisting of:

amino acids 1–60 deleted;
amino acids 61–122 deleted;
35:G→E; 37:S→Y;
35:G→E;
37:S→Y;
44, 47, 49:I . . . K . . . S→T . . . D . . . L;
52–54:T-G-A→S-S-P;
57,59:R . . . R→V . . . K;
64, 65:R-N→K-T;
64:R→K;
65:N→T
78, 79:K-G→T-D;
85,87:Q . . . D→R . . . N;
92, 94:K . . . Y→T . . . H;
94